United States Patent [19]

Puricelli

[11] Patent Number: 4,883,786

[45] Date of Patent: Nov. 28, 1989

[54] DERIVATIVES OF L-CARNITINE

[75] Inventor: Laura Puricelli, Brescia, Italy

[73] Assignee: Magis Farmaceutici Srl, Brescia, Italy

[21] Appl. No.: 282,938

[22] Filed: Dec. 8, 1988

Related U.S. Application Data

[63] Continuation of Ser. No. 124,405, Nov. 20, 1987, abandoned, which is a continuation of Ser. No. 750,253, Jul. 1, 1985, abandoned.

[30] Foreign Application Priority Data

Jun. 29, 1984 [IT] Italy ............................ 21655 A/84

[51] Int. Cl.$^4$ .................... C07C 101/30; A61K 31/19
[52] U.S. Cl. .................................... 514/47; 514/274; 514/554; 514/555; 536/27; 544/314; 562/567
[58] Field of Search .................. 562/567; 260/501.13, 260/501.12; 544/244, 314; 514/76, 274, 546, 551, 534, 554, 555; 536/27

[56] References Cited

U.S. PATENT DOCUMENTS

| | | | |
|---|---|---|---|
| 3,088,871 | 5/1963 | Pfeiffer | 514/554 |
| 3,903,147 | 9/1975 | Kyncl | 260/501.13 |
| 4,075,352 | 2/1978 | De Felice | 514/561 |
| 4,161,523 | 7/1979 | Weinstein | 514/30 |
| 4,401,827 | 8/1983 | Witt | 560/170 |
| 4,567,200 | 1/1986 | Tinti | 560/16 |
| 4,649,159 | 3/1987 | Fancelli | 514/556 |

FOREIGN PATENT DOCUMENTS

| | | | |
|---|---|---|---|
| 150688 | 8/1985 | European Pat. Off. | |
| 1356945 | 12/1961 | France | 260/501.13 |
| 310185 | 12/1965 | Spain | |
| 2077258 | 12/1981 | United Kingdom | 560/160 |

OTHER PUBLICATIONS

Goodman, "The Pharmacological Basis of Therapeutics", pp. 795-806 (1955).
Wilson, "Textbook of Organic Medical and Pharmaceutical Chemistry", p. 39 (1954).
"The Merck Index", 9th Ed., pp. 21, 892 & 893 (1976).
Hosein, Chem. Abstr., 67: 31250 (1967).

*Primary Examiner*—Michael L. Shippen
*Attorney, Agent, or Firm*—Stevens, Davis, Miller & Mosher

[57] ABSTRACT

Novel derivatives of L-carnitine or of L-acylcarnitines or of esters thereof, obtained by salification with suitable acids or acidic aminoacids, monosalified with potassium ion.

These derivatives show cardiotropic properties in the therapy of myocardial anoxia, of ischemia, of arrythmic syndromes, of cardiac failures in general and in cases of increased energy request due to fatigue at cardiac and muscular level.

2 Claims, No Drawings

DERIVATIVES OF L-CARNITINE

This application is a continuation of application Ser. No. 124,405, filed Nov. 20, 1987, now abandoned which in turn is a continuation of application Ser. No. 750,253, filed July 1, 1985, now abandoned.

DISCLOSURE

The present invention relates to new derivatives of L-carnitine or of L-acyl-carnitines or of esters thereof, to the process for preparing them, and to the use of them as therapeutical agents.

More precisely, the present invention relates to new compounds as prepared by condensing L-carnitine or an L-acyl-carnitine with an inorganic acid, an organic acid or an optically active acidic aminoacid, monosalified with potassium ion.

Said compounds have the following general formula:

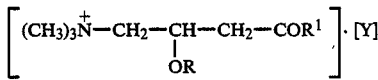

wherein R is either hydrogen or acyl, $R^1$ is either $O^-$ or alkoxy, and Y is an acid monosalified with potassium ion, belonging to the following group of acids: phosphoric acid, aspartic acid, acetylaspartic acid, glutamic acid, acetylglutamic acid, glutaric acid, α-ketoglutaric acid, orotic acid, succinic acid, phosphoserine, acetylphosphoserine, malic acid, pamoic acid, adenosinetriphosphoric acid.

The process for the preparation of the derivatives of L-carnitine or of L-acylcarnitines according to the present invention is characterized in that L-carnitine or L-acylcarnitine or the esters thereof are reacted in stoichiometric amounts with the acids and/or aminoacids salified with potassium ion belonging to the hereinabove reported group. The reaction is carried out in a suitable solvent, advantageously in water; the salt obtained is recovered by techniques well known to those skilled in the art, e.g. by freeze-drying or by evaporation of the solvent under reduced pressure.

The compounds according to the present invention show a very useful pharmacological activity:
in the treatment of potassic depletions
cardiac arrythmias
latent and manifested cardiac failure
acute or chronic myocardial ischemia—Angina pectoris
reintegration of the losses of carnitine and potassium in hemodialytical treatment.
neuromuscular asthenias.

In particular, said compounds show, as compared to L-carnitine and to its acyl derivatives, a stronger pharmacological effect, with more evident cardiotropic properties in the therapy of myocardial anoxia, of ischemia, of arrythmic syndromes, of cardiac failures in general, as well as in all those cases wherein the energy requirement at cardiac and muscular level has increased due to fatigue.

From the results obtained in the experimental investigation of the pharmacological activity of the compounds according to the present invention, a synergism of action of carnitine and of potassium ions is observed. The experimental study of the pharmacological activity of the compounds according to the present invention has been directed to the determination of acute toxicity, of the cardiokinetic effect on isolated heart, of the antiarrythmic effect and of the anti-failure effect, as it is reported hereinunder.

ACUTE TOXICITY

As the clinical use of the products according to the invention is foreseen to take place by oral way only, the acute toxicity thereof has been determined by such an administration way, using two animal species, i.e., mouse and rat.

Groups of Swiss mice and of Sprague-Dawley rats, of weights of 20–25 g and of 130–150 g respectively, fasting since the evening before the test, have been used.

Each group consisted of 20–10 male and 10 female-elements.

The products being investigated have been administered in the constant volume of 10 ml/kg in gum arabic at 2% in natural water, both in mouse and in rat species.

Doses have been tested of 1250–2500 and 5000 mg/kg both on mouse and on rat.

The animals have been kept under observation over 14 days, during which the arising of a possible toxic symptomatology and the mortality in each experimental group has been checked.

The products under investigation do not determine any mortality up to the dose of 5 g/kg. Moreover, during the 14 observation days, no toxic symptomatology appreciable on inspection was evidenced.

CARDIOKINETIC EFFECT ON ISOLATED HEART

Rabbit hearts isolated according to Langendorff have been perfused with an oxygenated Ringer solution.

The isometric contractions, the electrocardiogram and the coronary flow were recorded by using a polygraph. By removing oxygen from the perfusion liquid, a metabolic damage was induced in the cardiac muscle up to an 80% reduction of contraction force.

To the perfusion liquid oxygen was then added again, without the addition of any other substances (controls) or with the addition of the substance under examination (either carnitine or products according to the present invention). The force has been considered of the contraction of heart, expressing a positive inotropic effect, after 10 minutes from the interruption of the anoxia period (myocardium restoration).

The results have demonstrated that the products according to the invention induce a positive inotropic effect greater than that induced by carnitines, with statistically meaningful differences relatively to the controls.

ANTIARRYTHMIC EFFECT

The products according to the present invention show more evident antiarrythmic properties relatively to comparison carnitines.

ANTIFATIGUE EFFECT

In antifatigue tests the results have demonstrated that the products according to the present invention exert a greater antifatigue action than exerted by single carnitines.

Summing up, all the experimental data evidence the greater pharmacological effect of the substances according to the present invention than non-salified carnitines; the substances according to the present invention result hence to be particularly useful in the therapies as indicated above.

The following Examples are reported to illustrative, but not limitative, purposes of the process for the preparation of the derivatives of L-carnitine or of L-acylcarnitines according to the present invention.

EXAMPLE 1

Preparation of L-carnitine potassium succinate

An amount of 16.12 g of L-carnitine inner salt is dissolved in 30 ml of water; 15.62 g of potassium succinate dissolved in 10 ml of water are added, the mixture is stirred up to complete dissolution.

The solution is submitted to freeze-drying, 31.7 g of L-carnitine potassium succinate are obtained; the spectroscopic analyses confirm its structure.

M.W.=317.388 $C_{11}H_{20}NO_7K$.

| Elemental analysis | C | H | N | K |
|---|---|---|---|---|
| theoretical % | 41.59 | 6.3 | 4.41 | 12.28 |
| found % | 41.57 | 6.27 | 4.43 | 12.25 |

EXAMPLE 2

Preparation of L-carnitine potassium glutarate

An amount of 16.21 g of L-carnitine inner salt is dissolved in 30 ml of water; 17.02 g of potassium glutarate dissolved in 10 ml of water are added, the mixture is stirred up to complete dissolution.

The solution is submitted to freeze-drying; 33.2 g of L-carnitine potassium glutarate are obtained; the spectroscopic analyses confirm its structure.

| Elemental analysis | C | H | N | K |
|---|---|---|---|---|
| theoretical % | 43.45 | 6.63 | 4.22 | 11.76 |
| found % | 43.47 | 6.59 | 4.24 | 11.79 |

EXAMPLE 3

Preparation of L-carnitine potassium pamoate

An amount of 16.21 g of L-carnitine inner salt is dissolved in 30 ml of water; 37.84 g of potassium pamoate dissolved in 10 ml of water are added, the mixture is stirred up to complete dissolution.

The solution is submitted to freeze-drying, 54 g of L-carnitine potassium pamoate are obtained; the spectroscopic analyses confirm its structure.

| Elemental analysis | C | H | N | K |
|---|---|---|---|---|
| theoretical % | 66.71 | 5.56 | 2.59 | 7.22 |
| found % | 66.72 | 5.53 | 2.58 | 7.24 |

M.W. 539.628 $C_{30}H_{30}NO_9K$

EXAMPLE 4

Preparation of L-carnitine potassium aspartame

An amount of 16.21 g of L-carnitine inner salt is dissolved in 30 ml of water; 17.32 g of potassium aspartate dissolved in 10 ml of water are added. The mixture is stirred up to complete dissolution. The solution is submitted to freeze drying; 33.5 g of L-carnitine potassium aspartate are obtained; the spectroscopic analyses confirm its structure.

| Elemental analysis | C | H | N | K |
|---|---|---|---|---|
| theoretical % | 39.47 | 6.27 | 8.37 | 11.66 |
| found % | 39.46 | 6.29 | 8.39 | 11.66 |

M.W. 334.398 $C_{11}H_{21}N_2O_7K$.

EXAMPLE 5

Preparation of L-carnitine potassium α-ketoglutarate

An amount of 16.21 g of L-carnitine inner salt is dissolved in 30 ml of water; 18.42 g of potassium ≠0-ketoglutarate dissolved in 10 ml of water are added. The mixture is stirred up to complete dissolution.

The resulting solution is submitted to freeze-drying.

An amount of 34.6 g of L-carnitine potassium α-ketoglutarate is obtained; the spectroscopic analyses confirm its structure.

| Elemental analysis | C | H | N | K |
|---|---|---|---|---|
| theoretical % | 41.69 | 5.79 | 4.05 | 11.29 |
| found % | 41.67 | 5.61 | 4.07 | 11.32 |

M.W. 345.398 $C_{12}H_{20}NO_8K$.

EXAMPLE 6

Preparation of L-carnitine potassium phosphoserine

An amount of 16.21 g of L-carnitine inner salt is dissolved in 30 ml of water; 22.31 g of potassium phosphoserine dissolved in 10 ml of water are added.

The mixture is stirred up to complete dissolution.

The solution is submitted to freeze-drying. An amount of 38.5 g of L-carnitine potassium phosphoserine is obtained; the spectroscopic analyses confirm its structure.

| Elemental analysis | C | H | N | P | K |
|---|---|---|---|---|---|
| theoretical % | 31.21 | 5.72 | 7.28 | 8.06 | 10.14 |
| found % | 31.20 | 5.69 | 7.3 | 8.07 | 10.14 |

M.W. 384.378 $C_{10}H_{22}N_2O_9 PK$.

EXAMPLE 7

L-carnitine methyl ester potassium aspartate

An amount of 19.32 g of L-carnitine methyl ester is dissolved in 30 ml of anhydrous methanol, 17.11 g of potassium aspartate dissolved in 20 ml of anhydrous methanol are then added; the solution is evaporated, 36.5 g of L-carnitine methyl ester potassium aspartate being obtained.

The spectroscopic analyses confirm its structure.

| Elemental analysis | C | H | N | K |
|---|---|---|---|---|
| theoretical % | 39.3 | 6.8 | 7.64 | 10.64 |
| found % | 39.2 | 6.76 | 7.7 | 10.57 |

M.W. 366.4 $C_{12}H_{25}N_2O_8K$.

EXAMPLE 8

L-carnitine ethyl ester potassium aspartate

An amount of 20.72 g of L-carnitine ethyl ester is dissolved in 30 of absolute ethanol, 17.11 g of potassium aspartate in 20 ml of absolute ethanol are then added;

the solution is evaporated, 37.5 g of L-carnitine ethyl ester potassium aspartate being obtained. The spectroscopic analyses confirm its structure.

| Elemental analysis | C | H | N | K |
|---|---|---|---|---|
| theoretical % | 41 | 7.09 | 7.36 | 10.25 |
| found % | 40.8 | 7.1 | 7.32 | 10.26 |

M.W. 380.4 $C_{13}H_{27}N_2O_8K$.

EXAMPLE 9

L-carnitine ethyl ester potassium succinate

An amount of 20.72 g of L-carnitine ethyl ester is dissolved in 30 ml of absolute ethanol, they are then added to 15.62 g of potassium succinate dissolved in 20 ml of absolute ethanol; the solution is evaporated, thus 35 g being obtained of L-carnitine ethyl ester potassium succinate.

The spectroscopic analyses confirm its structure.

| Elemental analysis | C | H | N | K |
|---|---|---|---|---|
| theoretical % | 42.9 | 7.15 | 3.85 | 10.73 |
| found % | 42.7 | 7.13 | 3.82 | 10.74 |

M.W. 363.4 $C_{13}H_{26}NO_8K$.

EXAMPLE 10

L-carnitine methyl ester potassium glutarate

An amount of 19.32 g of L-carnitine methyl ester is dissolved in 30 ml of anhydrous methanol, 17.02 of potassium glutarate in 20 ml of anhydrous methanol being then added; the solution is evaporated, 26 g being obtained of L-carnitine methyl ester potassium glutarate being obtained.

The spectroscopic analyses confirm its structure.

| Elemental analysis | C | H | N | K |
|---|---|---|---|---|
| theoretical % | 44.4 | 7.66 | 7.4 | 10.3 |
| found % | 44.37 | 7.59 | 7.37 | 10.31 |

M.W. 378.3 $C_{14}H_{29}N_2O_8K$.

I claim:

1. A derivative of L-carnitine of the formula:

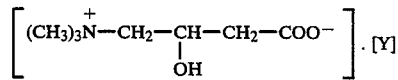

wherein Y is the monopotassium salt of an acid selected from the group consisting of: phosphoric acid, aspartic acid, acetylaspartic acid, glutamic acid, acetylglutamic acid, glutaric acid, β-keto-glutaric acid, orotic acid, succinic acid, phosphoserine, acetylphosphoserine, malic acid, pamoic acid and adenosinetriphosphoric acid.

2. A cardiotropic composition containing a cardiotropically effective amount of a derivative of L-carnitine according to claim 1, together with a pharmaceutically acceptable carrier.

* * * * *